United States Patent [19]

Babej et al.

[11] 4,078,083
[45] Mar. 7, 1978

[54] NOVEL PROSTANOIC ACIDS

[75] Inventors: Milos Babej, Frankfurt am Main; Wilhelm Bartmann, Neuenhain, Taunus; Ulrich Lerch, Hofheim, Taunus, all of Germany

[73] Assignee: Hoechst Aktiengesellschaft, Frankfurt am Main, Germany

[21] Appl. No.: 659,239

[22] Filed: Feb. 19, 1976

Related U.S. Application Data

[63] Continuation of Ser. No. 505,685, Sep. 13, 1974, abandoned.

[30] Foreign Application Priority Data

Sep. 17, 1973   Germany .............................. 2346706

[51] Int. Cl.$^2$ ..................... C07C 177/00; A61K 31/19
[52] U.S. Cl. ................................. 424/317; 260/347.3; 260/514 D; 260/520 R; 260/520 E; 542/429; 424/285

[58] Field of Search ................ 260/514 D, 468 D, 69; 424/317, 305

[56] References Cited

U.S. PATENT DOCUMENTS

| | | | |
|---|---|---|---|
| 3,870,747 | 3/1975 | Wendlen et al. ..................... | 260/468 |
| 3,873,607 | 3/1975 | Bernady et al. ..................... | 260/514 |

FOREIGN PATENT DOCUMENTS

| | | | |
|---|---|---|---|
| 9,095,941 | 9/1974 | Japan .................................... | 260/514 |

*Primary Examiner*—Robert Gerstl
*Attorney, Agent, or Firm*—Curtis, Morris & Safford

[57] ABSTRACT

New derivatives of prostanoic acids are described as well as a process for their manufacture. The new compounds show valuable pharmacological activities and can be used for treating e.g. asthma bronchiale, high blood pressure and edema.

2 Claims, No Drawings

NOVEL PROSTANOIC ACIDS

This is a continuation of application Ser. No. 505,685, filed Sept. 13, 1974, now abandoned.

The present invention relates to novel, not naturally occurring analogues of prostanoic acids and a process for their manufacture.

Prostaglandins are a group of natural substances which were isolated from different animal tissues. In mammals they are responsible for a great number of physiological actions. The natural prostaglandins have a carbon skeleton containing, in general, 20 carbon atoms and are distinguished, above all, by the major or minor content of hydroxyl groups or double bonds in the cyclopentane ring; (the structure and action of prostaglandins are described, i.a. in M. F. Cuthbert "The Prostaglandins, Pharmacological and Therapeutic Advances", William Heinemann Medical Books Ltd., London (1973)).

The syntheses of not naturally occurring analogues of prostanoic acids in which the great variety of the pharmacological actions of the natural prostanoic acids is differentiated, grow more and more important.

The present invention relates to novel, not naturally occurring analogues of prostanoic acids of the formula I

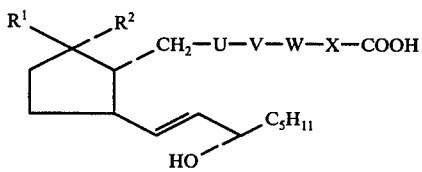

wherein

R¹ and R² together are oxygen or each is hydrogen or a hydroxyl group, R¹ and R² being different;

U is a (CH₂)ₘ-group, m being 0 to 5, a

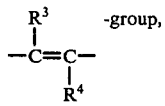

wherein R³ and R⁴ are identical or different and are hydrogen or alkyl of 1 to 5 carbon atoms, or a

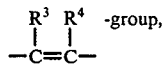

wherein R³ and R⁴ are identical or different and each is hydrogen or alkyl of 1 to 5 carbon atoms, but both cannot be hydrogen at the same time, when V and W each is a simple bond and X is (CH₂)₁₋₃;

V is a simple bond, oxygen or a radical of the formulae

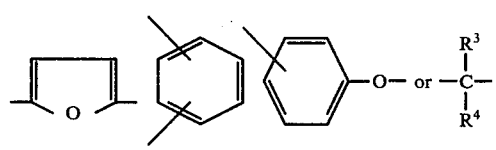

wherein R³ and R⁴ are identical or different and are hydrogen or alkyl of 1 to 5 carbon atoms, W is a simple bond or a radical of the formula

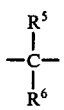

wherein R⁵ and R⁶ are identical or different and are hydrogen or alkyl of 1 to 5 carbon atoms;

X is a (CH₂)ₘ-group, wherein m is 0 to 5, and the physiologically acceptable salts thereof with inorganic or organic bases.

The present invention also relates to a process for the manufacture of compounds of the general formula I and to pharmaceutical preparations which contain these compounds as active substance.

The process of the invention comprises (a) carrying out a Retro-Dieckmann-condensation with a compound of the general formula II

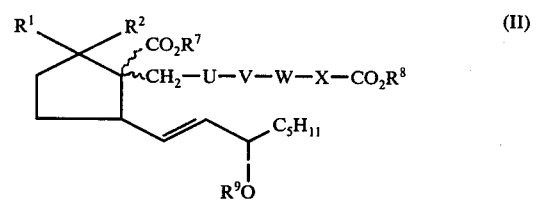

wherein

U, V, W and X are defined as above and

R¹ and R² together are oxygen,

R⁷ is alkyl of 1 to 5 carbon atoms,

R⁸ is alkyl of 1 to 5 carbon atoms,

R⁹ is optionally substituted alkyl of up to 20 carbon atoms, aryl, cycloalkyl of 5 to 8 carbon atoms, in which case a CH₂-group can be substituted by an oxygen atom, and subjecting the reaction product of the general formula III

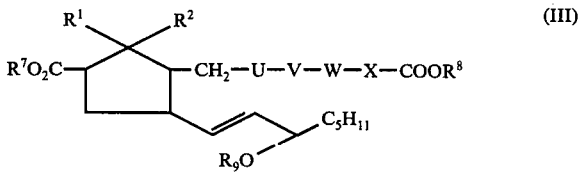

wherein the radicals R¹, R², R⁷, R⁸ and R⁹ and U, V, W and X are defined as in the formula II, to an alkaline saponification, a decarboxylation and an ether separation, in which operations compounds of the general formula Ia

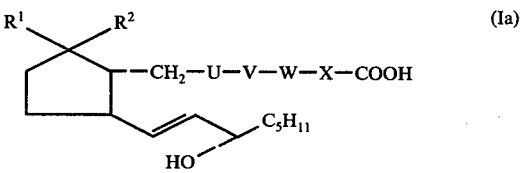

wherein R¹ and R² together are oxygen and U, V, W and X are defined as above, or their salts with inorganic and organic bases are obtained;

(b) reducing a compound of the general formula Ia with a complex metal hydride to a compound of the general formula Ib

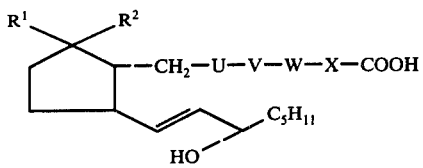

wherein $R^1$ and $R^2$ each is hydrogen or hydroxyl, $R^1$ and $R^2$ being different, and U, V, W and X are defined as above, and converting the reaction products optionally into the free acids or into the salts.

U is preferably a polymethylene chain of up to 3 $CH_2$-groups. Of the other radicals mentioned for U are preferred those in which $R^3$ or $R^4$ are an alkyl radical of up to 3 carbon atoms. The members X, W and V together form, preferably, an optionally branched chain of up to 10 members. If V is a phenylene or phenoxy radical, the other molecular parts may be in o-, m- or p-position to one another.

Starting compounds of the formula II which can be used in the process of the invention are described, for example, in the German Patent Application No. P 2,331,081.8 (HOE 73/F 171). They can be obtained according to the methods described therein.

This process comprises reacting, for example a compound of the formula IIa

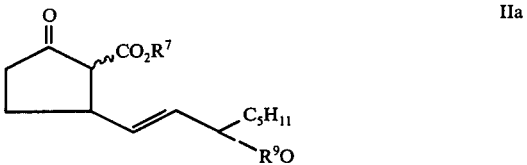

wherein $R^7$ and $R^9$ are defined as in the formula II, in an aprotic solvent in the presence of bases with a halogen carboxylic acid ester of the formula IIb

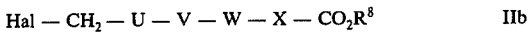

wherein U, V, W, X and $R^8$ are defined as in the formula II. The reaction is advantageously carried out at a temperature ranging between room temperature and 140° C in inert atmosphere. Suitable aprotic solvents are benzene, toluene or xylene. As base, there is preferably used anhydrous sodium ethylate or potassium tertiary butylate.

The compounds of the formula IIa can be obtained according to the Belgian Pat. No. 766,521.

The Retro-Dieckmann-condensation is preferably carried out in the presence of 1 to 1.5 moles of an alkali metal alcoholate in an alcohol (cf. Belgian Pat. No. 766,521) at room temperature up to 150° C for 1 to 16 hours in an inert gaseous atmosphere. The reaction product of the general formula III is subjected after the usual working up either directly or after chromatographic purification to an alkaline saponification, a decarboxylation or an acid ether separation (cf. also Belgian Pat. No. 766,521).

The compounds of the formula III are prepared as follows: Compounds of the general formula II (obtainable according to German Patent Application No. P 2,331,081.8 (HOE 73/F 171)) are dissolved in an anhydrous solution of 1 to 1.5 moles of an alkali metal alcoholate in an alcohol, preferably sodium ethylate in ethyl alcohol, and this solution is stirred with the exclusion of oxygen and moisture between 1 and 16 hours at a temperature ranging from 20° to 150° C. The reaction time and the reaction temperature depend on the reactivity of the compound II used. Generally the reaction is terminated at a temperature ranging from 50° to 90° C after 2 to 6 hours. Optionally, the reaction is brought to an end by heating in benzene or a xylene solution to a temperature of up to 150° C. Acidification follows under careful conditions, advantageously with acidic salts of polybasic acids and then working up in usual manner. The compounds of the general formula III are purified by chromatography on silica gel. An advantageous embodiment of the process of the invention for the manufacture of the compounds of the general formula Ia comprises saponifying not purified compounds of the general formula III directly with an alcoholic-aqueous solution of a base, isolating the dicarboxylic acids obtained after acidifying with dilute acids with an organic solvent from the aqueous phase, decarboxylating by heating for 1 to 4 hours in benzene or toluene to 80°-110° C in the manner usual for β-ketoacids and then separating the protective group of the alcohol function in 15-position by hydrolysis with an aqueous solution of an organic acid, for example 70aqueous acetic acid or 2% aqueous-alcoholic oxalic acid. The crude, not naturally occurring analogues of prostanoic acids of the general formula Ia can be purified by chromatography, for example with a cyclohexane/ethyl acetate mixture by adding acetic acid on silica gel. They are racemates and can be used as such. However, it is also possible to divide the compounds of the general formula Ia into their optical antipodes by the formation of salt with optically active bases.

The compounds of the formula Ia are reduced to compounds of the formula Ib according to method b with complex metal hydrides, advantageously with a metal boranate, for example zinc boron hydride in an organic solvent or an alkali metal boranate, such as sodium boron hydride in aqueous-organic phase or in an alcoholic solution.

The reaction products are worked up in usual manner and are purified by chromatography. The compounds so obtained are epimers with respect to the 9-position which can be used directly or which can be separated according to one of the usual separation methods for stereo isomers, for example with the aid of thin-layer-chromatography, to yield the epimers desired. When racemic compounds of the general formula Ia are used as starting material, racemic compounds (with respect to the 8 and 12-position) of the general formula Ib are obtained. The separation into the antipodes may follow with the formation of salt with optical bases.

The free acid is converted into a physiologically acceptable salt according to methods known per se. Suitable salts are, for example alkali metal salts or also triethanol ammonium or benzylammonium salts.

Compounds of the general formula I are to be named as optionally racemic prostanoic acids. (The nomenclature can be referred to inter alia in N. Andersen, Annals of the New York Academy of Sciences, Volume 180, Prostaglandins, page 14).

In addition to the examples given in the experimental part the process of the invention allows to obtain the following compounds:

9,15-α-dihydroxy-6-methyl-3-oxa-5-cis-13-trans-prostadienic acid 9,15-α-dihydroxy-5-methyl-3-oxa-5,13-trans-prostadienic acid 7-ethyl-15-α-hydroxy-9-oxo-13-trans-prostenoic acid 6,6-diethyl-15-α-hydroxy-9-oxo-13-trans-prostenoic acid 9,15-α-dihydroxy-4,4-dimethyl-13-trans-prostenoic acid 9,15-α-dihydroxy-2,2-dimethyl-3-oxa-13-trans-prostenoic acid.

The compounds of the general formula I are distinguished as compared with their closely related natural products by differentiated pharmacological effects. The compounds of the general formula Ia excel, for example by a marked spasmogen property.

For example, when a $CH_3$-group (experimental example 5, 6, 7, 8) is introduced into the 15-α-hydroxy-9-oxo-13-trans-prostenoic acid (experimental example 4, general formula Ia, $U = (CH_2)_5$, V, W, X = O) successively in 2-position, in 3, 4 and 5-position the spasmogen activity firstly decreases with the methyl branches in 2-position and then increases up to the 5-methyl compound.

15-α-Hydroxy-5-methyl-9-oxo-13-trans-prostenoic acid (experimental example 5) shows good spasmogen activity, a blood-pressure lowering activity which is reduced as compared with 15-α-hydroxy-9-oxo-13-trans-prostenoic acid and a good bronchodilating activity.

The pharmacological activity was determined in the following test arrangements:

Effect on the unstriped musculature (isolated rat stomach according to Vane, Br. J. Pharmac. Chemother., 12 344 (1957)).

The test was carried out on Wistar rats of both sexes having a weight of 200 to 220 g. The animals were killed by a blow onto the neck, the stomach was rapidly taken out and put into a Petri dish containing a pre-heated cancer solution. The fundus which is easily to be distinguished from the pyloric part because of its grey color, was separated and opened longitudinally by a longitudinal cut. Transversal cuts in counter-direction to each other led to a stripe which could be hung into the organ bath. The organ bath contained the usual cancer solution which was maintained at a temperature of 37° C and which was risen in bubbles with a mixture of 95% $O_2$ and 5% $CO_2$. A writing lever charged with 1 g served to register on a kymograph the contractions produced by adding the substance to be examined to the organ bath. The test criterion was the contraction occurring after the addition of the substance to be examined. The degree of activity was determined by comparing the contraction occurring after 600 ng/ml $PGA_2$. The values expressed in % with regard to the comparison preparation were used to draw a dose-activity-curve which allowed to determine the medium activity dose.

All substances were present as stock-solutions in absolute alcohol and were diluted to their final concentration with phosphate buffer (pH = 7.4).

Test of intravenously administered preparations for bronchospasmolytic activity according to Konzett-Rössler.

Except for irrelevant modifications, the test arrangement used largely corresponded to the description given by H. Konzett and R. Rössler, Arch. exp. Path. Pharmakol. 195, 71 (1940)). Test animals were male white Guinea pigs having a weight of 400 to 500 g. They were anesthesized with hexobarbital and urethane. All preparations to be administered were diluted with phosphate buffer (pH = 7.4) and administered in a volume of 0.1 ml.

Physiological or pharmacological effects were registered by measuring the air volume in the lung when the maximum blowing pressure was kept constant and a constant volume was maintained by respiration above atmospheric pressure. Capacity modifications in the respiratory tract show themselves in an increase or decrease of the air volume absorbed by the lung under the given constant blowing pressure. To produce a heavy bronchospasm acetylquoline or histamine were injected by the intravenous route. The dosage unit of the irritant was chosen such that an about 70 to 80% decrease of the absorption capacity of the lung was obtained. The substance to be examined was administered by the intravenous route in the V. jugularis. 30 seconds thereafter the already evaluated dosage unit of the irritant was injected once more. The medium inhibition dose was red off from the dose activity curve drawn either graphically or by means of regression analysis.

Test for the effect on the blood circulation

The hypotensive properties were examined in accordance with the methods described by Kannegiesser and Lee, Nature 229, 498 (1971).

Test animals were cats of both sexes having a weight of 2.0 to 3.0 kg.

The animals were anesthesized with pentobarbital in an amount of 1.7 to 2.8 mg/ml in 0.9% NaCl-solution as continuous infusion with 5 mg/kg/hour and pretreated with pentolinium (Ansolysen, May & Baker) with 10 mg/animal by the intraperitoneal route. The test substances were administered through the Vena jugularis. The blood pressure was measured in the A. carotis ext. directly and recorded by means of a Statham pressure sensor on a multi-channel recorder.

The maximum change of the systolic and diastolic blood pressure was measured in mm Hg.

All test preparations were present as stock solutions in absolute alcohol and were diluted to the end concentration immediately before the test beginning in phosphate buffer (pH = 7.4).

Compounds that show good bronchodilatory properties with diminished blood pressure action are of great importance for medicinal use, for example against the acute asthma attack.

The following Table 1 contains the spasmogen, blood-pressure lowering and bronchodilatory properties of a certain number of compounds coming within the scope of this invention, which are compared with each other.

| Experimental Example | Action on the unstriped musculature (isolated rat stomach) ED$_{50}$(μg/ml) | Bronchospasmolysis ID$_{50}$ (μg/kg i.v.) Histamine acetyl-quoline (Guinea pig) | Blood pressure (modifications in mm Hg) after 5 μ/kg i.v. (cat) |
| --- | --- | --- | --- |
| 4 rac. 15-α-Hydroxy-9-oxo-13-trans-prostenoic acid | 0.1 | 0.1 | 0.1 | −22/−27 at 0.5 μg/kg |
| 8 rac. 15-α-Hydroxy-2-methyl-9-oxo-13-trans-prostenoic acid | 1.3 | >10 | 0 |
| 7 rac. 15-α-Hydroxy-3-methyl-9-oxo-13-trans-prostenoic acid | 1.0 | 4.0 | 1.0 | −10/−20 |
| 6 rac. 15-α-Hydroxy-4-methyl-9-oxo-13-trans-prostenoic acid | 0.5 | 0.9 | 0.5 | −45/−50 |
| 5 rac. 15-α-Hydroxy-5-methyl-9-oxo-13-trans-prostenoic acid | 0.2 | 0.02 | 0.4 | −20/−30 |

The alcohols of the general formula Ib are distinguished by a good spasmogen action, for example the ED$_{50}$ in the isolated rat stomach for rac. 9,15-dihydroxy-3-oxa-5,13-trans-prostadienic acid (Example 29 A) is 3.1 μg/ml.

A further advantage of the compounds of the invention is their comparatively great stability towards acids and bases as compared with prostaglandins of the E and F series.

The present invention therefore allows the manufacture of compounds that are differentiated in their pharmacological properties compared to their natural analogues and are superior to the natural prostaglandins for the treatment of certain diseases.

Medicinal fields for use are, for example Asthma bronchiale, high blood pressure, edemas.

The compounds of the invention of the general formula I can be used in the form of their aqueous solutions or suspensions, optionally as salts with organic and inorganic bases, or as solutions in pharmacologically acceptable organic solvents, for example mono- or polyvalent alcohols, dimethylsulfoxide or dimethylformamide or N,N-dimethyl-acetamide, also in the presence of pharmacologically acceptable polymer carriers, for example polyvinyl pyrrolidone. Suitable dosage units are in addition to the usual galenic infusion or injection solutions also tablets. Further dosage unit forms are ointments, emulsions, suppositories or aerosoles.

For the oral dosage unit forms the active compounds are preferably mixed with substances known per se and brought into suitable dosage unit forms by methods known per se, for example tablets, dragees or gelatin capsules. As inert carriers, for example magnesium carbonate, lactose or corn starch with the addition of other substances, for example magnesium stearate can be used.

The dosage unit forms can be manufactured as dry or moist granule. The suitable dose is about 100 mg to 10 mg/day.

One dosage unit form contains preferably from 10 mg to 1 mg of a compound of the invention.

The compounds can be used alone or together with other pharmacologically active substances, for example diuretics or hypotensive agents or antiasthmatics.

The following Examples illustrate the invention:

EXAMPLE 1 rac. 15-α-Hydroxy-9-oxo-1,5-inter-p-phenylene-2,3,4-trinor-13-trans-prostenoic Acid a. rac. ethyl-10-ethoxycarbonyl-9-oxo-15-α-tetrahydropyranyloxy-1,5-inter-p-phenylene-2,3,4-trinor-13-trans-prostenoate 1.6 g (3.5 mmoles) of ethyl (5RS, 3'''SR)-1-[3'-(4''-ethoxycarbonylphenyl)-propyl]-2-oxo-5-[3'''-(2''''-tetrahydropyranyloxy)-trans-1'''-octenyl]-cyclo-pentanecarbonate and 4.15 ml of an anhydrous solution of sodium ethylate in ethanol were heated to boiling for 6 hours (85°–90° C bath temperature). The analysis of the reaction mixture by thin-layer chromatography showed, that the whole starting material was consumed (Al$_2$O$_3$-plates and cyclohexane/ether 1:1 were used as eluent). After the addition of 20 ml of dry toluene the ethanol was evaporated and cooled to −10° C. 4.5 ml of aqueous 2 N NaH$_2$PO$_4$-solution were added to the cooled solution while stirring. The organic phase was again washed with water and dried over MgSO$_4$. After evaporation 1.53 g of crude product were obtained which was chromatographed on 120 g of silica gel (Merck, 70–230 mesh ASTM).

Eluant:
200 ml cyclohexane/ethyl acetate/triethylamine 90:10:1
900 ml cyclohexane/ethyl acetate/triethylamine 80:20:1

Fractions of 8 ml were taken off. From fractions 52 to 130 870 mg of oily product were obtained.

Rf = 0.57 (cyclohexane/ethyl acetate/glacial acetic acid 40:60:1).

NMR: 7.65 ppm (4H, quadruplet); 5.5 ppm (2H) 4.65 ppm (1H) 4.5 to 3.4 ppm.

b. rac. 15-α-Hydroxy-9-oxo-1,5-inter-p-phenylene-2,3,4-trinor-13-trans-prostenoic acid 710 mg (1.3 mmoles) of rac. ethyl 10-ethoxycarbonyl-9-oxo-15-α-tetrahydropyranyloxy-1,5-inter-p-phenylene-2,3,4-trinor-13-trans-prostenoate were heated in 20 ml methanol and 14 ml 0.6 N sodium hydroxide solution for 6 hours while stirring to 60°–65° C. The methanol was evaporated on the rotary evaporator under reduced pressure and the remaining aqueous solution was washed twice with ether and then saturated with NaCl. Ether was superimposed and the solution was acidified with hydrochloric acid while cooling and stirring to pH 1 to 2. The aqueous phase was again extracted three times with ether, the combined organic phases were washed once with water and dried over anhydrous $Na_2SO_4$. After evaporating the ether, 620 mg of oily material were obtained which were heated with 7 ml of ethanol and 5 ml of 2% aqueous oxalic acid for 1 hour to 60°–65° C. After extracting the ethanol under reduced pressure the material was distributed between ether and water and the organic phase was evaporated over $MgSO_4$ after drying. The oily residue was chromatographed on 40 g of silica gel (Merck, 70–230 mesh ASTM) with cyclohexane/ethyl acetate/glacial acetic acid 60:40:1, fractions of 4 ml being collected. Fractions 57 to 76 yielded 260 mg of crystalline product after evaporation. m.p.: 110°–113° C.

Rf = 0.29 (cyclohexane/ethyl acetate/glacial acetic acid 40:60:1).
NMR: 7.65 ppm (4H, quadruplet), 6.85 ppm (2H, 5.6 ppm (2H) 4.1 ppm (1H).

EXAMPLE 2 rac. 15-Hydroxy-3-methyl-9-oxo-4,5,6-trinor-13-trans-prostenoic Acid a. rac. ethyl 10-ethoxycarbonyl-3-methyl-9-oxo-15-α-tetrahydropyranyloxy-4,5,6-trinor-13-trans-prostenoate 2.5 g (5 mmoles) of ethyl (5RS,3"SR)-1-(3'-ethoxycarbonyl-2'-methylpropyl)-2-oxo-5-[3"-(2'"-tetrahydropyranyloxy)-trans- 1"-octenyl]-cyclopentancarbonate were heated in 5.8 ml of 0.93 N sodium ethylate solution in absolute ethanol (5.4 mmoles) for 6 hours to 80° C and after the addition of 25 ml absolute toluene the solvent was distilled off up to the boiling temperature of 110° C (normal pressure). The solution was cooled to 0° C, 10 ml of 25% sodium dihydrogenphosphate solution and 20 ml of ice-cold, saturated sodium chloride solution were added and the solution was shaken four times with 100 ml of diethyl ether. The combined ether extracts were washed three times with 20 ml of $H_2O$, dried over $Na_2SO_4$ and the solvent was distilled off under reduced pressure. The residue was chromatographed on silica gel according to Merck (height of the column filling 22 cm, diameter 3.2 cm) and eluted with the following solvent mixtures dividing it into 310 fractions:

| Solvent | Fractions | |
|---|---|---|
| 750 ml cyclohexane/ethyl acetate/ triethyl amine 95:5:1 | 1 – 75 | 16 mg |
| | 76 – 130 | 60 mg |
| | 131 – 159 | 184 mg |
| 750 ml cyclohexane/ethyl acetate/ triethyl amine 90:10:1 | 160 – 310 | 1264 mg |
| 300 ml ethyl acetate | — | 584 mg |
| 300 ml methanol | — | 354 mg |

The fractions 131 to 159 contained 184 mg of slightly contaminated rac. ethyl 10-ethoxycarbonyl-3-methyl-9-oxo-15-α-tetrahydropyranyloxy-4,5,6-trinor-13-trans-prostenoate and the fractions 160 to 310 1264 mg of pure product.

b. rac. 3-Methyl-9-oxo-15-α-tetrahydropyranyloxy-4,5,6-trinor-13-trans-prostenoic acid 1.26 g of the above ester were stirred in 20 ml of methanol with 5.1 ml of 1 N NaOH for 48 hours at room temperature and for 5 hours at 50° C under argon, the solvent was distilled off under reduced pressure, the residue was additioned with 20 ml of saturated NaCl-solution, acidified with 2 N HCl up to pH 1 and extracted three times with 150 ml of diethyl ether. The combined ether extracts were washed neutral, dried over $Na_2SO_4$, concentrated and they yielded 1.18 g of yellow oil, which was heated under reflux in 50 ml of benzene for 1 hour and the solvent was extracted under reduced pressure.

c. rac. 15-α-Hydroxy-3-methyl-9-oxo-4,5,6-trinor-13-trans-prostenoic acid

The residue obtained in example 2b was heated with 18 ml of 2% oxalic acid solution in 30 ml of methanol for 2 hours to 50° C and the methanol was distilled off under reduced pressure. The aqueous residue was extracted three times with 150 ml of diethyl ether, the combined ether extracts were washed twice with 20 ml of water, dried over sodium sulfate and concentrated under reduced pressure. 1.023 g of residue were obtained. The brownish oil was chromatographed on silica gel according to Merck (height of the column filling 18 cm, diameter 2.2 cm).

| Solvent | Fractions | |
|---|---|---|
| 750 ml cyclohexane/ethyl acetate/ glacial acetic acid 66:33:1 | 1 to 160 | 56 mg |
| | 161 to 220 | 60 mg |
| | 221 to 245 | 320 mg |
| | 246 to 255 | 134 mg |
| 500 ml of cyclohexane/ethyl acetate/glacial acetic acid 59:40:1 | 256 to 350 | 303 mg |
| 300 ml methanol | | 42 mg |

The fractions 246 to 255 contained 135 mg of slightly contaminated rac. 15-α-Hydroxy-3-methyl-9-oxo-4,5,6-trinor-13-trans-prostenoic acid, and the fractions 256 to 350 contained 303 mg of this product.

Rf on silica gel plates according to Merck (cyclohexane/ethyl acetate/glacial acetic acid 60:40:1) = 0.1

| NMR in $CDCl_3$ | singulet | 7.55 ppm (2H) |
|---|---|---|
| | multiplet | 5.4 – 5.6 ppm (2H) |
| | multiplet | 4 – 4.15 ppm (1H) |

EXAMPLE 3 rac. 15-α-Hydroxy-3-oxa-9-oxo-5,13-trans-prostadienic Acid 1.76 g (3.5 mmoles) of ether (5RS,3"SR)-1-(6'-methoxycarbonyl-5'-oxa-trans-2'-hexenyl)-2-oxo-5-[3"-(2'"-tetrahydropyranyloxy)-trans-1"-octenyl]-cyclopentancarbonate were heated under argon with 3.6 ml (3.6 mmoles) of freshly prepared sodium ethylate solution for 3½ hours to 80° C. To the solution, cooled to 0° C, 20 ml of ice-cold $NaH_2PO_4$-solution were added, the solution was shaken with 500 ml of diethyl ether, washed with water, dried and concentrated. 1.8 g of a fair oil were obtained which was dissolved in 16 ml of methanol and stirred with 16 ml of 0.6 N NaOH for 3.5 hours at room temperature. The solution was concentrated under reduced pressure, acidified with 2N HCl to pH 2, extracted with 2 × 200 ml of diethyl ether, washed with water, dried and concentrated. 1.6 g of a yellow oil had formed that was boiled under reflux in 30 ml of benzene for 1 hour. The benzene was distilled off under reduced pressure and the residue was dissolved in 25 ml of ethanol and stirred with 25 ml of 2% oxalic acid solution for 6 hours at room temperature. The ethanol was distilled off under reduced pressure, the aqueous solution was extracted with 2 × 200 ml of diethyl ether, the ether phase was washed, dried and concentrated. 1.53 g of crude product had formed that were chromatographed on 50 g of silica gel according to Merck.

| Solvent | Fraction | |
|---|---|---|
| 300 ml of cyclohexane/ethyl acetate/ glacial acetic acid 80:20:1 | | |
| 300 ml of cyclohexane/ethyl acetate/ glacial acetic acid 70:30:1 | 1 – 240 | 157 mg |
| 300 ml of cyclohexane/ethyl acetate/ glacial acetic acid 60:40:1 | | |
| 350 ml of cyclohexane/ethyl acetate/ glacial acetic acid 60:40:1 | 241 – 400 | 690 mg |
| 350 ml of cyclohexane/ethyl acetate/ glacial acetic acid 50:50:1 | | |
| 350 ml of cyclohexane/ethyl acetate/ glacial acetic acid 50:50:1 | 401 – 550 | 143 mg |
| 400 ml of methanol | | 336 mg |

Substance in pure state: 690 mg.
Rf = 0.18 (silica gel, cyclohexane/ethyl acetate 70:35).
NMR (CDCl$_3$)
  6.1 ppm (2H, singulet)
  5.5–5.7 ppm (2H, multiplet)
  3.9–4.4 ppm (5H, singulet and multiplet)

EXAMPLE 4 rac. 15-α-Hydroxy-9-oxo-13-trans-prostenoic Acid 2.5 g (4.8 mmoles) of ether (5RS,3"SR)-1-(6'-ethoxycarbonylhexyl)-2-oxo-5-[3"-(2"'-tetrahydropyranyloxy)-trans-1"-octenyl]-cyclopentancarbonate were heated for 4 hours with 4.7 ml of 1.05 N (50 mmoles) of sodium ethylate solution in absolute ether to 80° C, 15 ml of absolute toluene were added and the solvent was distilled off under normal pressure until the boiling point of 110° C was reached. Working up followed as described in example 3 and 2.5 g of oily crude product were obtained. This product was stirred in 50 ml of ethanol with 9 ml of 0.6 N NaOH for 4 hours under argon. Working up followed as described in example 3, the yield was 2.2 g of oil that was heated under reflux without further purification in 30 ml of absolute benzene for 2 hours. The solvent was concentrated under reduced pressure, the residue was stirred in 50 ml of ethanol with 28 ml of 2% aqueous oxalic acid solution for 8 hours at room temperature and after working up in the same manner as described in example 3, 1.95 g of crude product were obtained which yielded after chromatography on silica gel by eluting with cyclohexane/ethyl acetate/glacial acetic acid 70:30:1 540 g of pure 15-α-hydroxy-9-oxo-13-trans-prostenoic acid beside 250 mg of slightly contaminated product.

NMR in CDCl$_3$
  6.5–6.6 ppm (singulet 2 protons)
  5.5–5.7 ppm (multiplet 2 protons)
  4–4.3 ppm (multiplet 1 proton).
By superimposing petrol ether, crystals were obtained which melted at 77°–81° C.
Rf = 0.1 (cyclohexane/ethyl acetate/glacial acetic acid 60:40:1).

EXAMPLE 5 rac. 15-α-Hydroxy-5-methyl-9-oxo-13-trans-prostenoic Acid

Product obtained in an analogous manner as described in example 3 from ethyl (5RS,3"SR)-1-(6'-ethoxycarbonyl-3'-methylhexyl)-2-oxo-5-[3"-(2"'-tetrahydropyranyloxy)-trans-1"-octenyl]-cyclopentancarbonate.

RF = 0.33 (cyclohexane/ethyl acetate/glacial acetic acid 40:60:1).
NMR: 7.6 ppm (2H), 5.55 ppm (2H), 4.2 ppm (1H).

EXAMPLE 6 rac. 15-α-Hydroxy-4-methyl-9-oxo-13-trans-prostenoic Acid

The test was carried out as described in example 3 starting from ethyl (5RS,3"SR)-1-(6'-ethoxycarbonyl-4'-methylhexyl)-2-oxo-5-[3"-(2"'-tetrahydropyranyloxy)-trans-1"-octenyl]-cyclopentanoate.

Rf = 0.31 (cyclohexane/ethyl acetate/glacial acetic acid 40:60:1).
NMR: 7.2 ppm (2H), 5.6 ppm (2H), 4.2 ppm (1H).

EXAMPLE 7 rac. 15-α-Hydroxy-3-methyl-9-oxo-13-trans-prostenoic Acid

The test was carried out in a manner described in example 3 starting from ethyl (5RS,3"SR)-1-(6'-ethoxycarbonyl-5'-methyl-hexyl)-2-oxo-5-[3"-(2"'-tetrahydropyranyloxy)-trans-1"-octenyl]-cyclopentancarbonate.

Rf = 0.34 (cyclohexane/ethyl acetate/glacial acetic acid 40:60:1).
NMR: 6.4 ppm (2H), 5.6 ppm (2H), 4.15 ppm (1H).

EXAMPLE 8 rac. 15-α-Hydroxy-2-methyl-9-oxo-13-trans-prostenoic Acid

The test was carried out as described in example 3 starting from ethyl (5RS,3"SR)-1-(6'-ethoxycarbonyl-heptyl)-2-oxo-5-[8"-(2"'-tetrahydropyranyloxy)-trans-1"-octenyl]-cyclopentanecarbonate.

Rf = 0.41 (cyclohexane/ethyl acetate/glacial acetic acid 40:60:1).
NMR: 6.75 ppm (2H), 5.6 ppm (2H), 4.1 ppm (1H).

EXAMPLE 9 rac. 2-Ethyl-15-α-hydroxy-9-oxo-13-trans-prostenoic Acid

The test was carried out as described in example 3 starting from ethyl (5RS,3"SR)-1-(2'-ethoxycarbonyl-octyl)-2-oxo-5-[3"-(2"'-tetrahydropyranyloxy)-trans-1"-octenyl]-cyclopentancarbonate.

Rf = 0.36 (cyclohexane/ethyl acetate/glacial acetic acid 40:60:1).
NMR: 5.6 ppm (2H), 5.4 ppm (2H), 4.1 ppm (1H).

EXAMPLE 10 rac. 2-Butyl-15-α-hydroxy-9-oxo-13-trans-prostenoic Acid 1.84 g (3.1 mmoles) of ethyl (5RS,3"-SR)-1-(6'-ethoxycarbonyldecyl)-2-oxo-5[3"-(2'''-tetrahydropyranyloxy)-trans-1"-octenyl]-cyclopentancarbonate were heated, as has been described in example 3, with 3.9 ml of 1 N sodium ethylate solution in ethanol for 5 hours to 80° C and after the addition of 25 ml of absolute toluene, the solvent was evaporated up to the boiling point of the toluene. After working up 1.84 g of crude product were obtained.

This product was stirred with 20 ml of 0.5 N NaOH in 20 ml of methanol for 48 hours at room temperature and for 72 hours at 60° C. After working up 685 mg of oil were obtained which yielded after saponification, ether separation and chromatographical separation as described in example 3, 240 mg of 2-butyl-15-α-hydroxy-9-keto-13-trans-prostenoic acid.

The NMR is CDCl$_3$ was nearly identical with the spectrum obtained in example 4.

Rf = 0.17 (cyclohexane/ethyl acetate/glacial acetic acid 60:40:1).

EXAMPLE 11 rac. 15-α-Hydroxy-9-oxo-2-nor-13-trans-prostenoic Acid a. rac. ethyl 10-ethoxycarbonyl-9-oxo-15-α-tetrahydropyranyloxy-2-nor-13-trans-prostenoate The test was carried out as described in example 1a starting from ethyl (5RS,3"-SR)-1-(5'-ethoxycarbonylpentyl)-2-oxo-5-[3"-(2'''-tetrahydropyranyloxy)-trans-1"-octenyl]-cyclopentancarbonate.

Rf = 0.23 (cyclohexane/ethyl acetate 85:15).
NMR: 5.6 ppm (2H), 4.65 ppm (1H), 4.4–3.3 ppm (7H).

b. rac. 15-α-Hydroxy-9-oxo-2-nor-13-trans-prostenoic Acid

The test was carried out in a manner analogous to that described in example 1b starting from rac. ethyl 10-ethoxycarbonyl-9oxo-15-α-tetrahydropyranyloxy-2-nor-13-trans-prostenoate.

Rf = 0.31 (cyclohexane/ethyl acetate/glacial acetic acid 40:60:1).
NMR: 6.35 ppm (2H), 5.65 ppm (2H), 4.2 ppm (1H).

EXAMPLE 12 rac. 15-α-Hydroxy-2-methyl-9-oxo-3-nor-13-trans-prostenoic Acid 1.9 g (3.6 mmoles) of ethyl (5RS,3"SR)-1-(5'-ethoxycarbonylhexyl)-2-oxo-5-[3"-(2'''-tetrahydropyranyloxy)-trans-1"-octenyl]-cyclopentancarbonate were heated with 4 ml of 1 N sodium ethylate solution in ethanol for 6 hours at 80° C and after the addition of 25 ml of toluene the solvent was distilled off under normal pressure up to the boiling point of 110° C. After working up as described in example 3 1.9 g of oil were obtained.

Saponification, decarboxylation and ether separation followed under the same conditions as described in example 3 which operations yielded after working up 1.55 g of crude product wherefrom by chromatography on silica gel and elution with cyclohexane/ethyl acetate/glacial acetic acid 60:40:1, 374 mg of pure rac. 15-α-Hydroxy-2-methyl-9-oxo-3-nor-13-trans-prostenoic acid were obtained. The NMR-spectrum was nearly identical with that obtained in example 4.

Rf = 0.14 (silica gel, cyclohexane/ethyl acetate/glacial acetic acid 60:40:1).

EXAMPLE 13 rac. 2-Ethyl-15-α-hydroxy-9-oxo-3-nor-13-trans-prostenoic Acid

The test was carried out as described in example 3 starting from ethyl (5RS,3"SR)-1-)-5'-ethoxycarbonylheptyl)-2-oxo-5-[3"-(2'''-tetrahydropyranyloxy)-trans-1"-octenyl]cyclopentanoate.

Rf = 0.33 (cyclohexane/ethyl acetate/glacial acetic acid 40:60:1).
NMR: 5.65 ppm (2H), 4.2 ppm (1H).

EXAMPLE 14 rac. 2-Butyl-15-α-hydroxy-9-oxo-3-nor-13-trans-prostenoic Acid

The test was carried out as described in example 3: 1.9 g (3.4 mmoles) of ethyl (5RS,3"SR)-1-(5'-ethoxycarbonylnonyl)-2-oxo-5-[3"-(2'''-tetrahydropyranyloxy)-trans-1"-octenyl]-cyclopentancarbonate were heated with 3.8 ml of 1 N sodium ethylate solution for 4 hours at 80° C and after the addition of 30 ml of absolute toluene the solvent was distilled off up to the boiling point of 110° C. After working up 1.7 g of a visquous oil were obtained. This oil was heated for 8 hours with 30 ml of methanol and 30 ml of 0.3 N sodium hydroxide solution to 50° C. After working up and heating for 1 hour in benzene 900 mg of oil were obtained which were heated with 30 ml of ethanol and 15 ml of 2% oxalic acid solution for 4 hours to 50° C. After reworking up 660 mg of crude product were obtained which yielded after chromatography on silica gel 245 g of pure rac. 2-butyl-15-α-hydroxy-9-oxo-3-nor-13-trans-prostenoic acid and a further 220 mg of slightly contaminated product. The NMR-spectrum was nearly identical with that obtained in Example 4.

Rf = 0.19 (silica gel, cyclohexane/ethyl acetate/glacial acetic acid 60:40:1).

EXAMPLE 15 rac. 15-α-Hydroxy-9-oxo-2,3-dinor-13-trans-prostenoic Acid a. rac. ethyl 10-carbethoxy-9-oxo-15-α-tetrahydropyranyloxy-2,3-dinor-13-trans-prostenoate The test was carried out as described in example 1a starting from ethyl (5RS, 3"SR)-1-(4'-ethoxycarbonyl-ω-butyl)-2-oxo-5-[3"-(2'''-tetrahydropyranyloxy)-trans-1"-octenyl]-cyclopentancarbonate.

Rf = 0.26 (cyclohexane/ethyl acetate 85:15).
NMR: 5.6 ppm (2H), 4.7 ppm (1H), 4.4–3.0 ppm.

b. rac. 15-α-Hydroxy-9-oxo-2,3-dinor-13-trans-prostenoic Acid

The test was carried out as described in example 1b starting from ethyl 10-carbethoxy-9-oxo-15-α-tetrahydropyranyloxy-2,3-dinor-13-trans-prostenoate.

M.P. 72° to 76° C.
Rf = 0.30 (cyclohexane/ethyl acetate/glacial acetic acid 40:60:1).
NMR: 6.55 ppm (2H), 5.6 ppm (2H), 4.1 ppm (1H).

EXAMPLE 16 rac.
15-α-Hydroxy-2-methyl-9-oxo-3,4-dinor-13-transprostenoic Acid

The reaction was the same as described in example 3 starting from ethyl (5RS,3"SR)-1-(4'-ethoxycarbonylpentyl)-2-oxo-5-[3"-(2'''-tetrahydropyranyloxy)-trans-1"-octenyl]-cyclopentancarbonate.

Rf = 0.32 (cyclohexane/ethyl acetate/glacial acetic acid 40:60:1).
NMR: 5.65 ppm (4H), 4.15 ppm (1H).

EXAMPLE 17 rac.
2-Ethyl-15-α-hydroxy-9-oxo-3,4-dinor-13-trans-prostenoic Acid 1.94 g (3.7 mmoles) of ethyl (5RS, 3"SR)-1-(4'-ethoxycarbonylhexyl)-2-oxo-5-[3"-2'''-tetrahydropyranyloxy)-trans-1"-octenyl]-cyclopentancarbonate were heated with 4.1 ml of sodium ethylate solution in ethanol for 5 hours to 80° C and after the addition of 25 ml of toluene the solvent was distilled off up to the boiling temperature of 110° C. The yield of crude product was 2 g of oil. This oil was heated with 35 ml of 0.3 N NaOH for 2 days in 35 ml of methanol to 50° C, worked up and, as has been described several times, heated in 30 ml of benzene for 1 hour to 80° C for decarboxylation. To separate the tetrahydropyranylether protective group stirring followed in 25 ml of ethanol with 23 ml of 2% oxalic acid solution for 10 hours at room temperature and after working up 1.7 g of a dark oil were obtained.
Chromatography on silica gel yielded after elution with cyclohexane/ethyl acetate/glacial acetic acid 70:30:1 295 mg of a visquious oil.

NMR-spectrum: similar to that obtained in example 4.
Rf = 0.11 (silica gel, cyclohexane/ethyl acetate/glacial acetic acid 60:40:1).

EXAMPLE 18 rac. 15-α-Hydroxy-9-oxo-2-homo-13-trans-prostenoic Acid

The reaction was the same as that described in example 3 starting from ethyl (5RS,3"SR)-1-(7'-ethoxycarbonylheptyl)-2-oxo-[3"-(2'''-tetrahydropyranyloxy)-trans-1"-octenyl]-cyclopentancarbonate.

Rf = 0.28 (cyclohexane/ethyl acetate/glacial acetic acid 40:60:1).
NMR: 6.3 ppm (2H), 5.6 ppm (2H), 4.1 ppm (1H).

EXAMPLE 19 rac.
15-α-Hydroxy-3-methyl-4-oxa-9-oxo-13-trans-prostenoic Acid

The reaction was effected as described in Example 3 starting from ethyl (5RS,3"SR)-1-(6'-ethoxycarbonyl-5'-methyl-4'-oxahexyl)-2-oxo-5-[3"-(2'''-tetrahydropyranyloxy)-trans-1"-octenyl]-cyclopentancarbonate.

Rf = 0.1 (silica gel, cyclohexane/ethyl acetate/glacial acetic acid 30:70:1).
NMR: 6 to 6.1 (2H, singulet), 5.5 to 5.7 ppm (2H, multiplet), 3.6 to 4.4 ppm (4H, broad signal).

EXAMPLE 20 rac. 15-α-Hydroxy-3-oxa-9-oxo-13-trans-prostenoic Acid

Reaction as described in example 3 starting from ethyl (5RS,3"SR)-1-(6'-methoxycarbonyl-5'-oxahexyl)-2-oxo-5-[3"-(2'''-tetrahydropyranyloxy)-trans-1"-octenyl]-cyclopentancarbonate.

Rf = 0.1 (silica gel, cyclohexane/ethyl acetate/glacial acetic acid 30:70:1).
NMR: (CDCl$_3$): 5.9 ppm (2H, singulet), 5.6–5.8 ppm (2H, multiplet), 4–4.2 ppm (3H, singulet with multiplet), 3.4–3.7 ppm (broad signal).

EXAMPLE 21 rac.
15-α-Hydroxy-3-oxa-9-oxo-5-cis-13-trans-prostadienic Acid

The reaction was analogous to that described in example 3 starting from ethyl (5RS,3"SR)-1-(6'-ethoxycarbonyl-5'-oxa-cis-2'-hexenyl)-2-oxo-5-[3"-(2'''-tetrahydropyranyloxy)-trans-1"-octenyl]-cyclopentancarbonate.

Rf = 0.5 (ethyl acetate, methanol 70:35, silica gel)
NMR:
6.85 ppm (2H, singulet)
5.7–5.9 ppm (4H, multiplet)
4–4.3 ppm (5H, singulet and multiplet)

EXAMPLE 22 rac.
15-α-Hydroxy-2-methyl-3-oxa-9-oxo-13-trans-prostenoic Acid

The reaction was carried out in an analogous manner to that described in example 3 starting from ethyl (5RS,3"SR)-1-(6'-ethoxycarbonyl-5'-oxa-heptyl)-2-oxo-5-[3"-(2'''-tetrahydropyranyloxy)-trans-1"-octenyl]-cyclopentancarbonate.

Rf = 0.13 (silica gel, cyclohexane/ethyl acetate/glacial acetic acid 30:70:1).
NMR:
6.4 ppm (2H, singulet)
5.5–5.7 ppm (2H, multiplet)
3.4–4.2 ppm (4H, broad signal)

EXAMPLE 23 rac.
15-α-Hydroxy-3-oxa-9-oxo-2-homo-5-cis-13-transprostadienic Acid

The reaction was carried out in an analogous manner to that described in example 3 starting from ethyl (5RS,3"SR)-1-(7'-methoxycarbonyl-5'-oxa-cis-2'-heptenyl)-2-oxo-5-[3"-(2'''-tetrahydropyranyloxy)-trans-1"-octenyl]-cyclopentanecarbonate.

Rf = 0.15 (silica gel, cyclohexane/ethyl acetate/glacial acetic acid 60:40:1).
NMR:
6.95 ppm (2H, singulet)
5.4–5.7 ppm (4H, multiplet)
3.9–4.4 ppm (5H, multiplet)

EXAMPLE 24 rac.
15-α-Hydroxy-9-oxo-4,7-inter-o-phenylene-5,6-dinor-13-trans-prostenoic Acid Reaction as described in example 3 starting from ethyl (5RS,3″SR)-1-[2′-(3″-ethoxycarbonylpropyl)-benzyl]-2-oxo-5-[3‴-(2″″-tetrahydropyranyloxy)-trans-1‴-octenyl]-cyclopentancarbonate.

Rf = 0.26 (cyclohexane/ethyl acetate/glacial acetic acid 40:60:1).
NMR: 7.1 ppm (4H), 6.7 ppm (2H), 5.45 ppm (2H).

EXAMPLE 25 rac.
15-α-Hydroxy-9-oxo-3,7-inter-p-phenylene-4,5,6-trinor-13-trans-prostenoic Acid The reaction was the same as described in example 3 starting from ethyl (5RS, 3″SR)-1-[4′-(2″-ethoxycarbonylether)-benzyl]-2-oxo-5-[3‴-(2″″-tetrahydropyranyloxy)-trans-1‴-octenyl]-cyclopentancarbonate.

Rf = 0.30 (cyclohexane/ethyl acetate/glacial acetic acid 40:60:1).
NMR: 7.1 ppm (4H), 6.8 ppm (2H), 5.5 ppm (2H), 4.05 ppm (1H).

EXAMPLE 26 rac.
15-α-Hydroxy-9-oxo-1,7-inter-p-phenylene-2,3,4,5,6-pentanor-13-trans-prostenoic Acid The reaction was analogous to that described in example 3 starting from ethyl (5RS,3″SR)-1-(4′-ethoxycarbonyl-benzyl)-2-oxo-5-[3″-(2‴-tetrahydropyranyloxy)-trans-1″-octenyl]-cyclopentancarbonate.

Melting point: 106° to 107° C.
Rf = 0.30 (cyclohexane/ethyl acetate/glacial acetic acid 40:60:1).
NMR: 7.65 ppm (4H, quadruplet), 6.7 ppm (2H), 5.55 ppm (2H), 4.05 ppm (1H), 2.97 ppm (2H).

EXAMPLE 27 rac.
15-α-Hydroxy-5-oxa-9-oxo-1,5-inter-p-phenylene-2,3,4-trinor-13-trans-prostenoic Acid Reaction as described in example 3 starting from ether (5RS,3″SR)-1-[2′-(4″-ethoxycarbonylphenoxy)-ethyl]-2-oxo-5-[3‴-(2″″-tetrahydropyranyloxy)-trans-1‴-octenyl]-cyclopentancarbonate.

Rf = 0.35 (cyclohexane/ethyl acetate/glacial acetic acid 40:60:1).
NMR: 7.45 ppm (4H, quadruplet), 6.3 ppm (2H), 5.65 ppm (2H), 4.15 ppm (3H).

EXAMPLE 28 rac.
1,7-inter-(2,5-furylidene)-15-α-hydroxy-9-oxo-2,3,4,5,6-pentanor-13-trans-prostenoic Acid Reaction as described in example 3 starting from ethyl (5RS,3″SR)-1-(5′-ethoxycarbonylfurfuryl)-2-oxo-5-[3‴-(2″″-tetrahydropyranyloxy)-trans-1″-octenyl]-cyclopentancarbonate.

Rf = 0.13 (silica gel, cyclohexane/ethyl acetate/glacial acetic acid 30:70:1).
NMR in $CDCl_3$:
7.1–7.3 ppm (1H, dublet)
6.5 ppm (2H, singulet)
6.2 ppm (1H, dublet)
5.5–5.7 ppm (2H, multiplet)
4–4.1 ppm (1H, multiplet).

EXAMPLE 29 rac. 9,15-α-Hydroxy-3-oxa-5,13-trans-prostenoic Acids A and B 140 mg of rac. 15-α-hydroxy-3-oxa-9-oxo-5,13-transprostadienic acid were dissolved in 20 ml of methanol and in the course of 1.5 hours three times 150 mg of sodium boron hydride were added. The reaction solution was adjusted to pH 7 with glacial acetic acid, the solvent was distilled off under reduced pressure, the residue was acidified in 10 ml of $H_2O$ with 2 N HCl to pH 1 and extracted three times with each 100 ml of diethyl ether. The combined ether extracts were washed with water, dried over sodium sulfate and the solvent was distilled off under reduced pressure.

The reaction product (140 mg) was a mixture of two epimers with respect to the position of the hydroxy groups in 9-position. The epimer (fraction A) running more rapidly over silica gel was maintained pure by chromatography on 4 g of silica gel according to Merck.

Using 200 ml of cyclohexane/ethyl acetate, 1:9 there were eluted:

(A) 30 mg Rf = 0.45 (silica gel, ethyl acetate/methanol 70:35) and using 200 ml of ethyl acetae/methanol 8:2.
(B) 44 mg showing two spots in the DC (mixture of both epimers)
Rf = 0.45 (silica gel, ethyl acetate/methanol 70:35)
Rf = 0.39.
NMR of fraction A:
5.5–5.8 ppm (4H, multiplet)
4.7 ppm (3H, singulet)
4–4.2 ppm (6H, singulet and multiplet)
NMR of fraction B:
5.5–5.8 ppm (4H, multiplet)
5.2 ppm (3H, singulet)
4–4.1 ppm (6H, singulet and multiplet)

EXAMPLE 30 rac. 9.15-α-Dihydroxy-2,3-dinor-13-trans-prostenoic Acid

To 110 mg (0.28 mmole) of rac. 15-α-Hydroxy-9-oxo-2,3-dinor-13 -trans-prostenoic acid in 5 ml of isopropanol were added portionwise 130 mg of sodium boron hydride (development of hydrogen). After being allowed to dwell over night, evaporation followed under reduced pressure at a bath temperature of 30° C and to the residue, 20 ml of ether and 10 ml of saturated sodium chloride solution were added. Under cooling and stirring the whole was acidified with 1 N HCl carefully to pH 2. The aqueous phase was again extracted twice with ether, the combined organic phases were washed with saturated sodium chloride solution, dried and concentrated. The residue (115 mg) was chromatographed on 10 g of $SiO_2$. The eluent was cyclohexane/ethyl acetate/glacial acetic acid 40:60:1.

The more rapid isomer has an Rf-value of 0.20 (cyclohexane/ethyl acetate/glacial acetic acid 40:60:1), the slowlier one has an Rf-value of 0.17 in the same eluent. NMR-spectrum of the isomer mixture: 5.5 ppm (2H, multiplet), 5.3 ppm (2H, singulet), 4.1 ppm (2H, multiplet).

EXAMPLE 31
rac.
9,15-α-Dihydroxy-1,5-inter-p-phenylene-2,3,4-trinor-13-trans-prostenoic Acid The reaction was carried out in a manner analogous to that described in example 29 starting from rac. 15-α-hydroxy-9-oxo-1,5-inter-p-phenylene-2,3,4-trinor-13-trans-prostenoic acid.

Rf-value of the more rapid isomer: 0.23 (cyclohexane/ethyl acetae/glacial acetic acid 40:60:1).
NMR-spectrum: 7.6 ppm (4H, $A_2B_2$-type), 5.5 ppm (2H), 4.4–3.9 ppm (5H).
Slowlier isomer: m.p. 124° to 126° C
Rf-value = 0.19 (cyclohexane/ethyl acetate/glacial acetic acid 40:60:1).
NMR: 7.6 ppm (4H, $A_2B_2$-type), 5.45 ppm (2H), 4.3–3.7 ppm (5H).

EXAMPLE 32
rac.
9,15-α-Dihydroxy-3-oxo-5-cis-13-trans-prostadienic Acid

In an analogous manner to that described in example 29 there were obtained from 150 mg of rac. 15-α-hydroxy-3-oxa-9-oxo-5-cis-13-trans-prostadienic acid 82 mg of rac. 9,15-α-dihydroxy-3-oxa-5-cis-13-trans-prostadienic acid.

Rf = 0.43 (silica gel, ethyl acetate/methanol 70:35)
NMR in $CDCl_3$:
 5.4–5.7 ppm (4H, multiplet)
 5 ppm (3H, singulet)
 3.9–4.3 ppm (6H, singulet and multiplet).

EXAMPLE 33
rac.
9,15-α-Dihydroxy-2-methyl-3-nor-13-trans-prostenoic Acid

In an analogous manner as described in example 29 there were obtained from 70 mg of rac. 15-α-hydroxy-2-methyl-9-oxo-3-nor-13-trans-prostenoic acid 56 mg of rac. 9,15-α-dihydroxy-2-methyl-3-nor-13-trans-prostenoic acid.

Rf = 0.07 (silica gel, cyclohexane/ethyl acetate/glacial acetic acid (60:40:1).
NMR in $CDCl_3$:
 5.4–5.7 ppm (2H, multiplet)
 5.0 ppm (3H, singulet)
 3.9–4.3 ppm (2H, broad signal).

EXAMPLE 34
rac.
2-Ethyl-9,15-α-dihydroxy-3,4-dinor-13-trans-prostenoic Acid

In an analogous manner as described in example 29 there were obtained from 70 mg of rac. 2-ethyl-15-α-hydroxy-9-oxo-3,4-dinor-13-trans-prostenoic acid 40 mg of rac. 2-ethyl-9,15-α-dihydroxy-3,4-dinor-13-trans-prostenoic acid.

Rf = 0.07 (silica gel, cyclohexane/ethyl acetate/glacial acetic acid 60:40:1).
NMR in $CDCl_3$:
 5.4–5.7 ppm (2H, multiplet)
 5.0 ppm (3H, singulet)
 3.9–4.3 ppm (2H, broad signal)

EXAMPLE 35
rac.
9,15-α-Dihydroxy-3-oxa-2-homo-5-cis-13-trans-prostenoic Acid In an analogous manner as described in example 29 the product was obtained from rac. 15-α-hydroxy-3-oxa-9-oxo-2-homo-5-cis-13-trans-prostenoic acid.

Rf = 0.55 (silica gel, ethyl acetate/methanol 70:35)
NMR in $CDCl_3$:
 5.4–5.7 ppm (4H, multiplet)
 5.0 ppm (3H, singulet)
 3.9–4.3 ppm (6H, multiplet)

EXAMPLE 36
rac.
15-α-Hydroxy-5-methyl-9-oxo-5-trans-13-trans-prostadienic Acid The product was obtained according to the method described in example 3 from ethyl (5RS, 3"SR)-1-(6'-ethoxycarbonyl-3'-methyl-trans-2'-hexenyl)-2-oxo-5-[3"-(2'''-tetrahydropyranyloxy)-trans-1"-octenyl[-cyclopentancarbonate.

NMR in $CDCl_3$: 6.2 ppm (2H, 5.6 ppm (2H), 5.1 ppm (1H), 4.1 ppm (1H).

EXAMPLE 37
rac. 9,15-α-Dihydroxy-5-methyl-13-trans-prostenoic Acid

The product was obtained in an analogous manner as described in example 30 from rac. 15-α-hydroxy-5-methyl-9-oxo-13-trans-prostenoic acid.

NMR in $CDCl_3$: 5.5 ppm (5H), 4.2 ppm (2H).

EXAMPLE 38
rac. 15-α-Hydroxy-6-methyl-9-oxo-13-trans-prostenoic Acid

The product was obtained in an analogous manner as described in example 3 from ethyl (5RS,3"SR)-1-(6'-ethoxycarbonyl-2'-methylhexyl)-2-oxo-5-[3"-(2'''-tetrahydropyranyloxy)-trans-1"-octenyl]-cyclopentancarbonate. Rf-value and NMR-spectrum: practically identical with that described in example 5.

EXAMPLE 39 rac. 15-α-Hydroxy-4-ethyl-9-oxo-13-trans-prostenoic Acid

The product was obtained in an analgous manner to that of example 3 from ethyl (5RS,3"SR)-1-(6'-ethoxycarbonyl-4'-ethylhexyl)-2-oxo-5-[3"-(2'''-tetrahydropyranyloxy)-trans-1"-octenyl]-cyclopentancarbonate.

Rf = 0.35 (cyclohexane/ethyl acetate/glacial acetic acid 40:60:1).

EXAMPLE 40 rac. 15-α-Hydroxy-5-ethyl-9-oxo-13-trans-prostenoic Acid

The product was obtained in an analogous manner as described in example 3 from ethyl (5RS,3"SR)-1-(6'-ethoxycarbonyl-3'-ethylhexyl)-2-oxo-5-[3"-(3'''-tetrahydropyranyloxy)-trans-1"-octenyl]-cyclopentancarbonate.

NMR in CDCl$_3$: 6.3 ppm (2H), 5.6 ppm (2H), 4.1 ppm (1H).

EXAMPLE 41 rac. 15-α-Hydroxy-6-ethyl-9-oxo-13-trans-prostenoic Acid

The product was obtained in an analogous manner as described in example 3 from ethyl (5RS,3"SR)-1-(6'-ethoxycarbonyl-2'-ethylhexyl)-2-oxo-5-[3"-(2'''-tetrahydropyranyloxy)-trans-1"-octenyl]-cyclopentancarbonate.

Rf = 0.32 (cyclohexane/ethyl acetate/glacial acetic acid 40:60:1)

EXAMPLE 42 rac. 15-α-Hydroxy-9-oxo-4-oxa-1,4-inter-o-phenylene-2,3-dinor-13-trans-prostenoic Acid The product was obtained in an analogous manner as described in example 3 from ethyl (5RS,3"SR)-1-[3'-(2"-ethoxycarbonylphenoxy)-propyl]-2-oxo-5-[3''''-tetrahydropyranyloxy)-trans-1''''-octenyl]-cyclopentancarbonate.

NMR in CDCl$_3$:
6.8–8.2 ppm (4H, multiplet)
6.4 ppm (2H, singulet)
5.7 ppm (2H)
4.2 ppm (3H).

What is claimed is:

1. 15-α-hydroxy-5-methyl-9-oxo-13-trans-prostenoic acid and physiologically acceptable salts thereof with an organic or inorganic base.

2. A pharmaceutical composition for treating bronchial spasms, said composition comprising a bronchospasmolytic amount of a compound as claimed in claim 1 in combination with a pharmaceutical carrier.

* * * * *